United States Patent [19]

Laney

[11] Patent Number: 5,648,513

[45] Date of Patent: Jul. 15, 1997

[54] O-ACYL SERINES

[76] Inventor: Judith Wolfe Laney, 12018 Auth La., Silver Spring, Md. 20902

[21] Appl. No.: 562,086

[22] Filed: Nov. 22, 1995

Related U.S. Application Data

[62] Division of Ser. No. 428,706, Apr. 25, 1995, abandoned, which is a division of Ser. No. 118,188, Sep. 9, 1993, Pat. No. 5,431,904.

[51] Int. Cl.$^6$ .................... C07C 229/60; C07C 69/84; C07C 69/68
[52] U.S. Cl. ............... 560/49; 560/74; 560/104; 560/179; 560/266
[58] Field of Search .................. 560/74, 104, 49, 560/179, 266

[56] References Cited

U.S. PATENT DOCUMENTS

| 3,107,252 | 10/1963 | Lubowe | 260/309.5 |
| 4,089,942 | 5/1978 | Bore et al. | 424/47 |
| 5,213,791 | 5/1993 | Lyon et al. | 424/65 |
| 5,431,904 | 7/1995 | Laney | 424/65 |

FOREIGN PATENT DOCUMENTS

| 7-179328 | 7/1995 | Japan . |
| 348210 | 12/1967 | U.S.S.R. . |
| 592631 | 9/1947 | United Kingdom . |
| 1446584 | 8/1976 | United Kingdom . |

OTHER PUBLICATIONS

Bengel et al., J. Chem. Soc., pp. 846–853 (1963).
Adkins et al., J.A.C.S., vol. 76, pp. 147–152 (1954).
Bore et al., Chem. Abs., No. 87(16):122645f (1977).
Hirata et al., Chem. Abs., No. 113(8):64563v (1989).
Inoue, Chem. Abs., No. 111(16):140544r (1988).
Klosa, Chem. Abs., No. 78(13):84815r (1973).
Mitomo, CHem. Abs., No. 83(4):32923h (1975).
Ono et al., Chem. Abs., No. 108(22):188398m (1987).
Sagarin, Cosmetics Science and Technology, pp. 717, 733 and 1202–1211 (1957).
Sato et al., Chem. Abs., No. 110(16):141224c (1987).
Takasago Perfumery Co., Ltd., Chem. Abs., No. 103(24):200711g (1985).

*Primary Examiner*—Bernard Dentz
*Attorney, Agent, or Firm*—Burns, Doane, Swecker & Mathis, LLP

[57] ABSTRACT

The invention relates to a method of suppressing human body malodor by utilizing a deodorant composition containing a competitive substrate for the enzymatic creation of axillary body malodor. The compound is present in a dermatologically acceptable vehicle, and in an amount effective to reduce the conversion of malodor producing precursor. The present invention also relates to novel O-acylated serine compounds and method for the production thereof.

6 Claims, No Drawings

O-ACYL SERINES

This application is a divisional of application Ser. No. 08/428,706, filed Apr. 25, 1995, now abandoned, which is a divisional of application Ser. No. 08/118,188, filed Sep. 9, 1993, now U.S. Pat. No. 5,431,904.

BACKGROUND OF THE INVENTION

The present invention relates to deodorants, a method of suppressing human body odor, compounds useful as deodorants and method for the production thereof.

The ecorine and apocrine sweat glands are the structures of the human body responsible for sweat. The apocrine glands become active at puberty and produce an odorless proteinaceous secretion. Axillary bacteria act on the apocrine secretions to produce the pungent odor known as axillary malodor.

Current deodorants are generally of three types: odor maskers, antiperspirants, and germicides. Despite the many disclosures in the art pertaining to deodorant compositions, current products are not sufficient to suppress odor in a significant proportion of the population, particularly during periods of "stress." There remains a need for new deodorant compositions and methods which are effective, safe and economical.

SUMMARY OF THE INVENTION

The present invention relates to a deodorant composition comprising a compound which is capable of serving as an alternative substrate to the naturally occurring malodor producing precursor. The compound is present in a dermatologically acceptable vehicle, and in an amount effective to reduce the conversion of malodor producing precursor.

The present invention further relates to a method for suppressing body malodor which includes the application to the skin of the deodorant composition of the present invention.

The present invention also relates to novel O-acylated serine compounds and a method for the production thereof.

DETAILED DESCRIPTION OF THE INVENTION

The current invention is a novel method of suppressing body odor by the topical application of compounds which compete with the naturally occurring malodor producing precursor. The compounds are O-acylated serine derivatives. Deodorant compositions containing at least one compound from the specified group of O-acylated serine derivatives in an effective concentration will serve to suppress axillary malodor when applied to the underarm. Tests indicate that these compositions significantly attenuate the body odors formed in the axilla. In a preferred embodiment, the o-acylated serine derivatives may generate pleasant odors in the axilla concomitant with suppressing the malodor.

Axillary malodor is generated by certain skin bacteria in the presence of apocrine secretion. Two strains of bacteria which produce axillary malodor when incubated with human apocrine secretions are Staphylococcus and several Coryneform isolates. Production of human axillary malodor can be assayed from these strains of bacteria by incubating cells with apocrine secretions collected from human axilla that has been sterilized in a phosphate buffer at pH 6.8. The volatile malodor compound is extracted into chloroform and smelled after spotting on filter paper.

The conversion of the naturally occurring apocrine precursor to axillary malodor occurs within the bacterial cells. Extracts of bacteria are capable of converting the precursor to the malodor compound in an enzymatic process. The enzyme which is designated as the malodor-forming enzyme has been found to be a pyridoxal phosphate dependent amino acid lyase. The enzyme acts to cleave amino acids with the general structure HOOC—CH(NH$_2$)—CH$_2$—X where X is S—R or O—R. The products of the reaction are pyruvate, ammonia, and XH.

The naturally occurring apocrine precursor to axillary malodor is a sulfur containing amino acid. It has now been found that the production of axillary malodor is blocked if an alternative substrate for the malodor-forming enzyme is provided, so that the alternative substrate is cleaved instead of the apocrine precursor. The alternative substrates produce either a neutral odor or a pleasant odor upon cleavage.

Certain amino acids and amino acid analogues can serve as deodorants in this fashion, i.e., these amino acids and amino acid analogues serve as alternative substrates for the malodor-forming enzyme and produce a neutral or pleasant odor. As stated above, the malodor-forming enzyme cleaves amino acids and amino acid analogues having the general structure, HOOC—CH(NH$_2$)—CH$_2$—X where X is S—R or O—R.

In the present invention, O-acylated serine derivatives are employed with an R group which results in the production of neutral or pleasant odors. The general structure of the O-acyl serines of the present invention is HOOC—CH(NH$_2$)—CH$_2$—O—C(O)—R. The R group may be a) a branched or straight alkyl, alkenyl, or alkynyl chain of one to about seventeen carbon atoms that is unsubstituted or substituted with one or more halo, hydroxyl, amino, nitro, amide, carboxyl, or phenyl that is unsubstituted or substituted with one or more halo, hydroxyl, amino, nitro, amide, or carboxyl; or b) a phenyl that is unsubstituted or substituted with one or more halo, hydroxyl, amino, nitro, or carboxyl, or an aliphatic carbon chain of one to about eight carbon atoms that is unsubstituted or substituted with one or more halo, hydroxyl, amino, nitro, amide, carboxyl, or phenyl that is unsubstituted or substituted with one or more halo, hydroxyl, amino, nitro, amide, or carboxyl.

Suitable substrates include compounds such as O-succinyl serine, O-benzoyl serine, O-phenylacetyl serine, O-malonyl serine, O-acetyl serine, O-oleoyl serine, O-palmitoyl serine, O-cinnamoyl serine, O-p-aminobenzoyl serine, O-lactoyl serine, O-salicyloyl serine, O-sarcosinoyl serine, O-2-ethyl hexanoyl serine, and the like.

For example, the malodor-forming enzyme cleaves O-benzoyl serine (i.e., where X is O-benzoyl) to produce non-odorous benzoic acid. Suitable R groups of the O-acyl serines of the present invention include —CH=CH—C$_6$H$_5$ which is cleaved to produce cinnamic acid; —C$_6$H$_4$NH$_2$ which is cleaved to produce p-aminobenzoic acid; —CH(OH)C$_3$ which is cleaved to produce lactic acid; —C$_6$H$_4$OH which is cleaved to produce salicylic acid; —C$_2$H$_4$NH$_2$ which is cleaved to produce sarcosine; and —CH(C$_2$H$_5$)—(CH$_2$)$_3$—CH$_3$ which is cleaved to produce 2-ethyl hexanoic acid.

Suitable O-acyl serines of the present invention can be prepared by the following procedure. Initially, protected serine is esterified with the desired R group compound, such as by esterification mediated by dicyclohexylcarbodiimide. The intermediate product may then be purified according to conventional purification techniques and recrystallized. The recrystallized intermediate product is then hydrogenated in the presence of an appropriate catalyst, e.g., palladium/carbon, to remove the protecting groups and yield the corresponding O-acyl serine.

The presence of the O-acyl serine in adequate quantities will compete with the natural precursor and at least reduce, if not almost entirely prevent the conversion of the natural precursor to the malodor compound.

In addition, when certain of these alternative substrates are cleaved, pleasant odors are produced. These o-acylated serine derivatives are generally those in which the R group is an aromatic or branched chain aliphatic group. The acid that results from cleavage is pleasant smelling. The compound O-phenylacetyl serine is converted to phenylacetic acid, a compound that smells of honey, which is an example of such a cleavage product.

The presence of an alternative substrate such as the above compound in moderate quantities competes with the natural precursor which is present in low quantities, typically about one nanomole/axilla. Such competition almost completely prevents the malodor precursor from being converted. These compounds therefore serve as deodorants.

Although deodorancy is the most important concern for the consumer of underarm products, many also choose a product with antiperspirant activity. Current antiperspirant compounds, which are aluminum salts, also function as deodorants by virtue of their germicidal properties. Thus, if desired, the deodorants of the present invention can be employed with the antiperspirant salts well known in the art. In such formulations, the C-acylated serine derivatives can be incorporated into a deodorant or antiperspirant formulation along with an antiperspirant salt, wherein the antiperspirant salt may be employed in a perspiration reducing effective concentration, e.g., 6 to 30% or in a deodorant effective concentration, e.g., 1 to 6%.

The antiperspirant salt used in the present invention may be any of those which contain aluminum, either alone or in combination with other materials such as zirconium. Typical aluminum salts, although not all-inclusive, include:

Aluminum chlorohydrate;
Aluminum sesquichlorohydrate;
Aluminum dichlorohydrate;
Aluminum chlorohydrex PG or PEG;
Aluminum sesquichlorohydrex PG or PEG;
Aluminum dichlorohydrex PG or PEG;
Aluminum zirconium trichlorohydrate;
Aluminum zirconium tetrachlorohydrate;
Aluminum zirconium tetrachlorohydrex PG or PEG;
Aluminum zirconium pentachlorohydrate;
Aluminum zirconium octachlorohydrate;
Aluminum zirconium trichlorohydrex-gly;
Aluminum zirconium tetrachlorohydrex-gly;
Aluminum zirconium pentachlorohydrex-gly;
Aluminum zirconium octachlorohydrex-gly;
Aluminum zirconium chloride;
Aluminum zirconium sulfate;
Potassium aluminum sulfate;
Sodium aluminum chlorohydroxylacetate;
Aluminum bromohydrate.

In general, the active antiperspirant salt is present in the same amounts at which such materials are employed in prior art compositions. As a general rule, such compositions contain from about 3% to about 30%, preferably from about 10% to about 25%, of the active antiperspirant salt component.

In order to further illustrate the present invention and the advantages thereof, the following specific examples are given. It is understood that these examples are intended only to be illustrative without serving to limit the scope of the present invention.

EVALUATION OF O-ACYL SERINES THAT PRODUCE NEUTRAL OR ODORLESS PRODUCTS

EXAMPLE 1

As a representative of the class, O-benzoyl serine was evaluated and was found to be effective as a substrate of the malodor enzyme at concentrations of 0.5 millimolar and above. When tested as described above for the ability to block malodor formation by bacterial cells, the minimum concentration needed for complete inhibition was 25 millimolar.

EXAMPLE 2

O-succinyl serine was evaluated and was found to be effective as a substrate of the malodor enzyme at concentrations of 1 millimolar and above. When tested as described above for the ability to block malodor formation by bacterial cells, the minimum concentration needed for complete inhibition was 150 millimolar.

EVALUATION OF O-ACYL SERINES THAT PRODUCE A PLEASANT ODOR

EXAMPLE 3

O-phenylacetyl serine was tested as described above for the ability to inhibit malodor in vitro while producing in its place a pleasant odor. The compound blocked malodor production at a concentration of 25 millimolar while producing a pleasant, honey-like fragrance.

PREPARATION OF O-BENZOYL SERINE

EXAMPLE 4

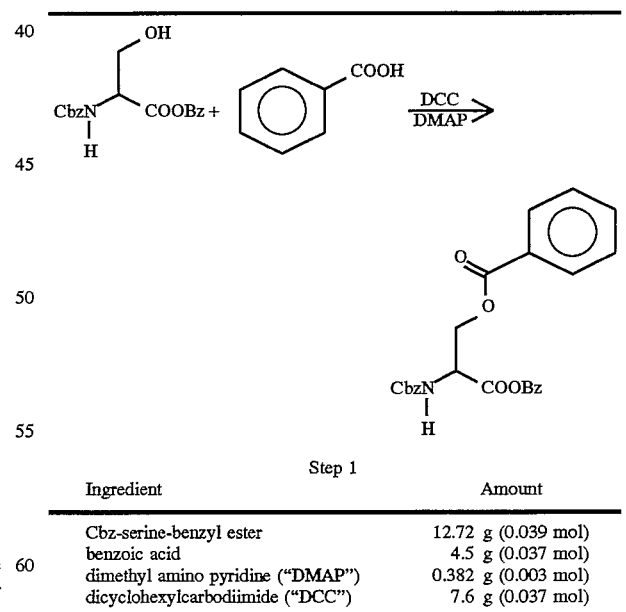

Step 1

| Ingredient | Amount |
|---|---|
| Cbz-serine-benzyl ester | 12.72 g (0.039 mol) |
| benzoic acid | 4.5 g (0.037 mol) |
| dimethyl amino pyridine ("DMAP") | 0.382 g (0.003 mol) |
| dicyclohexylcarbodiimide ("DCC") | 7.6 g (0.037 mol) |

Dissolve benzoic acid in $CH_2Cl_2$ (200 mL). Add carbobenzyloxy-serine-benzyl ester and DMAP. Cool on ice bath. Add DCC. Keep on ice bath for 5 minutes, then remove ice and stir at room temperature under $N_2$ for 4 hours.

Filter to remove precipitated dicyclohexyl urea. Concentrate to dryness, then re-dissolve in $CH_2Cl_2$ and filter to remove any new precipitate. Wash twice with 1N HCl then once with saturated $NaHCO_3$. Dry organic layer over $MgSO_4$ and concentrate in vacuo. The crude product is recrystallized from 2-propanol to give carbobenzyloxy-benzoyl-serine-benzyl ester as a white solid, m.p. 94°–95° C.

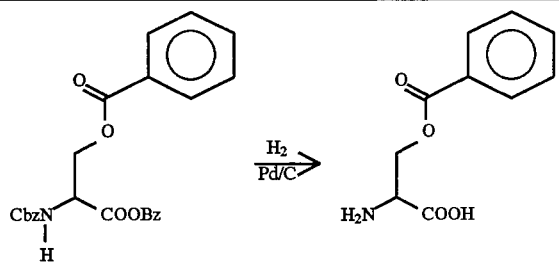

Step 2

| Ingredient | Amount |
|---|---|
| Cbz-PhCO-serine-benzyl ester | 10.8 g (0.25 mol) |
| 10% Pd/carbon | 3 g |

The protected amino acid, carbobenzyloxy-benzoyl-serine-benzyl ester, is placed in a large flask and dissolved in methanol (500 mL) with stirring. Stirring is stopped, and the Pd/C catalyst added slowly. The vessel is purged with $H_2$ for 1 minute. The reaction is then stirred under $H_2$ (1 atmosphere) overnight. The reaction mixture is filtered through a pad of Celite, the pad is rinsed with MeOH, and the combined filtrate and rinsings are concentrated in vacuo to give the product O-benzoyl serine as a white solid, m.p. 125–130 (decomposed).

FORMULATIONS FOR DEODORANT USE

The concentration of O-acylated serine derivative employed in topical applications should be consistent with efficacy, economy and safety. The O-acylated serine derivatives of the present invention are employed in a malodor precursor competing amount in a dermatologically acceptable vehicle, and are efficacious at concentrations between about 5 micromolar and about 500 millimolar, i.e., about 0.01% to about 10% by weight. The most preferred range is from about 50 micromolar to about 100 millimolar. This constitutes a weight percent of about 0.1% to about 2% by weight as the most preferred range of active ingredient.

If desired, the O-acylated serine derivatives of the present invention can also be employed in combination with an antiperspirant salt. In such case, the O-acylated serine derivative is added to a standard deodorant or antiperspirant formulation containing the antiperspirant salt in the same concentrations as set forth above.

Examples of various formulations are given below:

EXAMPLE 5

| Deodorant Stick | |
|---|---|
| Ingredient | % by weight |
| propylene glycol | 78 |
| sodium stearate C-1 | 7.9 |

-continued

| Deodorant Stick | |
|---|---|
| Ingredient | % by weight |
| fragrance | 0.1 |
| water | 13 |
| O-phenylacetyl serine | 1 |

Procedure: Mix propylene glycol and sodium stearate C-1 at room temperature and stir. Increase the temperature to about 70° C. and continue agitation to obtain a clear and uniform solution. Add the water followed by the O-phenylacetyl serine. Lower the temperature to 55° C. and add the fragrance. Pour into molds and cool to room temperature.

EXAMPLE 6

| Deodorant Roll-On Emulsion | |
|---|---|
| Ingredient | % by weight |
| hydrogenated palm oil glycerides and sodium cetyl sulfate | 3.0 |
| steareth-7 | 1.0 |
| octyldodecanol | 4.0 |
| glyceryl laurate | 2.0 |
| octyl palmitate | 4.0 |
| dimethicone | 1.0 |
| propylparaben | 0.1 |
| methylparaben | 0.2 |
| imidazolidinyl urea | 0.3 |
| glycerin | 5.0 |
| allantoin | 0.5 |
| PEG-35 lanolin | 0.5 |
| fragrance | 0.3 |
| 2 wt. % O-benzoyl serine in 80% propylene glycol/20% water at neutral pH | 78.1 |

Procedure: Mix and stir the ingredients except the fragrance at 80° C. Decrease the temperature to 40° C. and add the fragrance. Decrease the temperature to room temperature.

EXAMPLE 7

| Aerosol Deodorant | |
|---|---|
| Ingredient | % by weight |
| zinc phenolsulfonate | 1.7 |
| quaternium 18 hectorite | 1.0 |
| dioctyl succinate | 10.0 |
| SDA 40 ethanol, anhydrous | 20.0 |
| fragrance | 0.1 |
| 1 wt. % O-succinyl serine in 50% ethanol/water at neutral pH | 10.0 |
| propellant | 57.2 |

Procedure: Dissolve all ingredients in the alcohol, add the propellant, and cold or pressure fill.

EXAMPLE 8

| Roll-On Antiperspirant and Deodorant | |
|---|---|
| Ingredient | % by weight |
| PPG-15 stearyl ether | 4.0 |
| steareth-21 | 0.6 |
| steareth-2 | 2.6 |

7

-continued

| Roll-On Antiperspirant and Deodorant | |
|---|---|
| Ingredient | % by weight |
| aluminum zirconium pentachlorohydrate, 10:1 (a 25% solution) | 32.0 |
| fragrance | 0.1 |
| 1.8 wt % O-oleoyl serine in 80% propylene glycol/water at neutral pH | 60.7 |

Procedure: Mix all the ingredients except the fragrance at 70° C. with agitation. Add the fragrance at 45° C. Stir and cool to room temperature.

EXAMPLE 9

| Aerosol Antiperspirant and Deodorant | |
|---|---|
| Ingredient | % by weight |
| O-palmitoyl serine | 1.0 |
| isopropyl myristate | 13.4 |
| aluminum chlorohydrate | 10.0 |
| quaternium-18 hectorite | 0.8 |
| SDA 40 ethanol, anhydrous | 0.8 |
| fragrance | 0.1 |
| propellant | 73.9 |

Procedure: Mix the isopropyl myristate and quaternium-18 hectorite together for 30 minutes with an Eppenbach Homomixer. Add aluminum chlorohydrate and mix 15 minutes. Add the O-palmitoyl serine and SDA 40 and mix 10 minutes. Homogenize the suspension using a Manton-Gaulin homogenizer set at 6000 psi. Add fragrance and mix on a Hobart Mixer set at moderate speed. Mix 10 minutes. Charge with propellant.

EXAMPLE 10

| Stick Antiperspirant and Deodorant | |
|---|---|
| Ingredient | % by weight |
| aluminum chlorohydrate | 16.0 |
| SDA 40 ethanol, anhydrous | 30.0 |
| sorbitol, 70% | 3.0 |
| sodium stearate C-1 | 5.0 |
| sodium ceteth-13 carboxylate | 3.0 |
| stearyl alcohol | 1.0 |
| cyclomethicone | 15.0 |
| fragrance | 0.1 |
| 2 wt. % O-malonyl serine in 80% propylene glycol/water at neutral pH | 26.9 |

Procedure: Mix the aluminum chlorohydrate, SDA 40 ethanol and the O-malonyl serine and heat to 65° C. Add sorbitol and then sodium stearate C-1 and sodium ceteth-13 carboxylate, and mix until a complete solution is obtained. Add the remaining ingredients and mix for 5 minutes. Cool to 50° C. and add to containers.

Other objects, features and advantages of the present invention will become apparent from the foregoing detailed description and accompanying examples. It should be understood, however, that the detailed description and specific examples, while indicating various embodiments of the invention, are given by way of illustration only, since various changes and modifications within the spirit and scope of the invention will become apparent to those skilled in the art from this detailed description.

What is claimed is:

1. A compound of the structure

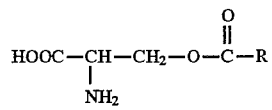

wherein R is selected from the group consisting of —CH=CH—$C_6H_5$,

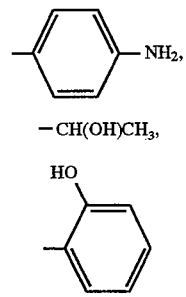

—CH(OH)$CH_3$, and —CH($C_2H_5$)—$(CH_2)_3$—$CH_3$.

2. A compound according to claim 1 of the formula HOOC—CH($NH_2$)—$CH_2$—O—C(O)—CH(OH)$CH_3$.

3. A compound according to claim 1 of the formula HOOC—CH($NH_2$)—$CH_2$—O—C(O)—CH($C_2H_5$)—$(CH_2)_3$—$CH_3$.

4. A compound according to claim 1 of the formula

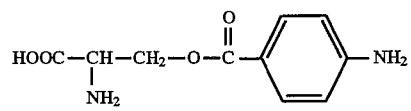

5. A compound according to claim 1 of the formula

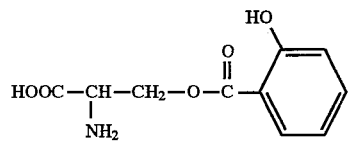

6. A compound of the structure

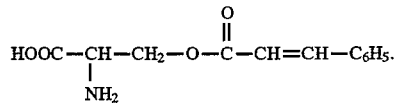

* * * * *